United States Patent
Srinivasan et al.

(10) Patent No.: US 10,176,188 B2
(45) Date of Patent: Jan. 8, 2019

(54) AUTOMATED DICTIONARY CREATION FOR SCIENTIFIC TERMS

(71) Applicant: Tata Consultancy Services Limited, Maharashtra (IN)

(72) Inventors: Rajgopal Srinivasan, Hyderabad (IN); Thomas Joseph, Hyderabad (IN); Venkat Raghavan Ganesh Sekar, Hyderabad (IN); Saipradeep Govindakrishnan Vangala, Hyderabad (IN); Naveen Sivadasan, Yeddumailaram (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 160 days.

(21) Appl. No.: 13/752,620

(22) Filed: Jan. 29, 2013

(65) Prior Publication Data

US 2013/0218849 A1 Aug. 22, 2013

(30) Foreign Application Priority Data

Jan. 31, 2012 (IN) .......................... 298/MUM/2012

(51) Int. Cl.
G06F 17/30 (2006.01)
G06F 19/28 (2011.01)
G06F 17/27 (2006.01)

(52) U.S. Cl.
CPC .... G06F 17/30156 (2013.01); G06F 17/2735 (2013.01); G06F 17/30731 (2013.01); G06F 19/28 (2013.01)

(58) Field of Classification Search
CPC ........... G06F 17/2735; G06F 17/30156; G06F 19/28; G06F 17/30303; G06F 17/30734; G06F 17/30737; G06F 17/30731

(Continued)

(56) References Cited

U.S. PATENT DOCUMENTS 6,173,253 B1 1/2001 Abe et al.
8,667,022 B2 * 3/2014 Iwamoto ................ G06Q 10/10
707/791

(Continued)

FOREIGN PATENT DOCUMENTS

WO 03/077151 A2 9/2003

OTHER PUBLICATIONS

"Wolfram Mathematica Tutorial Collection: Core Language". 2008. Wolfram Research. p. 117 and 229.*

(Continued)

Primary Examiner — Taelor Kim
Assistant Examiner — Jesse P Frumkin
(74) Attorney, Agent, or Firm — Seed IP Law Group LLP (57) ABSTRACT

Systems and methods for automated creation of a dictionary of scientific terms are described herein. Initially, input data is filtered to obtain a primary file having a plurality of term-ID pairs with each term-ID pair having a unique term ID and a scientific term. Further, a remove-term file is generated based on one or more term-ID pairs identified from the primary file such that the scientific terms of each term-ID pair corresponds to one of additional terms, frequent scientific terms, and undesirable terms. At least one term-ID pair from among the one or more term-ID pairs is altered to obtain a modified term-ID pair based on modification rules. The modified term-ID pair is added to an add-term file and a modified file is obtained based on the remove-term file and the add-term file. Duplicate term-ID pairs present in the modified file are removed to obtain the dictionary of scientific terms.

20 Claims, 2 Drawing Sheets

(58) Field of Classification Search
USPC .......................................................... 707/692
See application file for complete search history.

(56) References Cited

U.S. PATENT DOCUMENTS

| | | | | |
|---|---|---|---|---|
| 8,943,023 | B2* | 1/2015 | Sorenson, III | .... G06F 17/30345 707/610 |
| 2003/0233251 | A1* | 12/2003 | Haskell | ............... G06F 17/2735 705/2 |
| 2006/0026204 | A1* | 2/2006 | Campbell | ......... G06F 17/30731 |
| 2006/0242191 | A1* | 10/2006 | Kutsumi | ............. G06F 17/2735 |
| 2007/0299697 | A1* | 12/2007 | Friedlander | ........... G06F 19/322 705/3 |
| 2008/0082483 | A1* | 4/2008 | Lim | .................. G06F 17/30616 |
| 2011/0320459 | A1* | 12/2011 | Chisholm | ............. G06F 17/218 707/748 |
| 2012/0310969 | A1* | 12/2012 | Heidasch | .......... G06F 17/30734 707/769 |

OTHER PUBLICATIONS

McMahon, Lee E. SED: a Non-interactive Text Editor. Bell Telephone Laboratories, 1979.*

Balakrishnan, Rama, Julie Park, Kalpana Karra, Benjamin C. Hitz, Gail Binkley, Eurie L. Hong, Julie Sullivan, Gos Micklem, and J. Michael Cherry. "YeastMine-an integrated data warehouse for *Saccharomyces cerevisiae* data as a multipurpose tool-kit." Database 2012 (2012).*

"Using the *Saccharomyces* Genome Database (SGD) for analysis of genomic information." Current Protocols in Bioinformatics (2011): 1-20.*

"Tata Consultancy Services: BioAppliance Platform". (2012). TCS Design Services p. 08 12.*

*Saccharomycles* Genome Database FAQ, date unknown [captured by archive.org on Oct. 8, 2011] yeastgenome.org, https://web.archive.org/web/20111008031700/http://yeastgenome.org/SGD-FAQ.shtml.*

The PathQuery API—InterMine documentation, Jan. 3, 2010, readthedogs.org, http://intermine.readthedocs.org/en/latest/api/pathquery/.*

SGD Video Tutorials: Yeastmine, date unknown [captured by archive.org on 28 Jan. 28, 2013]m yeastgenome.org, https://web.archive.org/web/20130128194323/http://www.yeastgenome.org/help/video-tutorials/yeastmine.*

YeastMine: Creating and Using Gene Lists, posted on Sep. 1, 2011 [as stated in SGD Video Tutorials: YeastMine], vimeo.com, https://vimeo.com/28472237?lite=1.*

Parai et al., "The Lexicon Builder Web service: Building Custom Lexicons from two hundred Biomedical Ontologies," AMIA 2010 Symposium Proceedings, pp. 587-591, Nov. 2010.

Schuemie et al., Evaluation of techniques for increasing recall in a dictionary approach to gene and protein name identification, Sciencedirect (Journal of Biomedical informatics 40), 2007, 9 pages.

Fluck et al., ProMiner: Recognition of Human Gene and Protein Names using regularly updated Dictionaries, Proceedings of the Second BioCreative Challenge Evaluation Workshop, 2007, pp. 149-151, Madrid.

Mitsumori et al., Gene/protein name recognition based on support vector machine using dictionary as features, BMC Bioinformatics, May 24, 2005, 6(Suppl 1):S8, 10 pages.

Fundel et al., Gene and protein nomenclature in public databases, BMC Bioinformatics, Aug. 9, 2006, 7:372, 13 pages.

Genia Tagger—part-of-speech tagging, shallow parsing, and named entity recognition for biomedical text, http://www-tsujii.is.s.u-tokyo.ac.jp/GENIA/tagger/, Oct. 20, 2006, 3 pages.

* cited by examiner

AUTOMATED DICTIONARY CREATION FOR SCIENTIFIC TERMS

TECHNICAL FIELD

The present subject matter relates, in general, to the field of natural sciences and, in particular, to automated creation of dictionary of scientific terms.

BACKGROUND

Natural science has been a field of active research for ages with new researches being conducted on a regular basis. Each new discovery results in unveiling of new characteristics of known or unknown environmental elements sometimes leading to renaming or evolution of new scientific terms related to environmental elements, such as genomes, proteins, and chemicals. For instance, study of a particular organism's genome, such as human genome and mouse genome, is a field of active research today. An understanding of genome variations may enable researchers to fully understand the issues of genetic susceptibility and pharmacogenomics of drug response for all individuals as well as personalized molecular diagnostic tests. Thus, a vast amount of biomedical literature related to genomic research has been published to assist the researchers in their work. However, in order to use the data, for example, while formulating a new hypothesis or to interpret experimental results, a researcher may need to go through the vast biomedical literature. Studying such a huge volume of data is often a cumbersome and time consuming task, and therefore data mining tools may be implemented. For example, in order to formulate new hypothesis for a particular organism's genome, a researcher may need to identify and extract data related to various genes associated with the particular genome.

Conventionally, researchers followed a process of pattern identification to identify gene data, i.e., data related to a particular gene associated with a specific genome. Pattern identification required a researcher to identify gene data related to a particular gene using a gene pattern associated with the gene, by extracting from various literature sources all documents having the gene pattern. Documents containing the gene pattern may then be studied to identify and use the gene data contained in the documents. For example, during studies related to, say, tumors in human, the researchers may need to identify data related to a tumor suppressor protein that in humans is encoded by a TP53 gene. In such a case using the conventional process of pattern recognition would require the researchers to use a gene pattern of the TP53 gene to access all documents that contain the gene pattern and study the same to identify the gene data related to the TP53 gene. However, owing to the long length of the gene patterns, using such a method of gene data identification may not be efficient in terms of time and resource requirements.

In recent years, various named entity recognition techniques have been implemented to search scientific data, such as protein data related to various proteins, gene data related to a particular gene, chemical and drug data related to a particular chemical or drug, based on a scientific term, such as gene name of the gene. Searching scientific data based on the scientific term reduces the time and sources required for the search as the scientific terms are typically smaller and simpler to search than the conventional methods. For example, searching gene data based on the gene name reduces the time and sources required for the search as the gene names are typically smaller and simpler to search than the conventional methods using the gene patterns. However, identifying a gene based on the gene name may not be feasible owing to various reasons, such as no fixed nomenclature for naming a gene. In absence of a common nomenclature, different researchers may use different gene names to refer to a particular gene while publishing white papers or storing gene data related to the particular gene in a gene database. For instance, a person may name a gene, she researched about, using her birth date, while another person may name the same gene on his own name. Searching gene data based on the gene names may thus require either complex text mining tools or manual intervention to filter and identify various gene names related to a particular gene. Searching other scientific data based on the scientific term may not be feasible due to similar complexities involved.

SUMMARY

This summary is provided to introduce concepts related to automated creation of a dictionary of scientific terms, which are further described below in the detailed description. This summary is not intended to identify essential features of the claimed subject matter nor is it intended for use in determining or limiting the scope of the claimed subject matter.

Method(s) and a system(s) for automated creation of a dictionary of scientific terms are described herein. In one embodiment, input data may be filtered to obtain a primary file having a plurality of term-ID pairs where each of the plurality of term-ID pair includes a unique term ID and a scientific term associated with the unique term ID. The primary file may be analyzed to identify one or more term-ID pairs from among the plurality of term-ID pairs. The one or more term-ID pairs may be identified such that the scientific terms of each of the one or more term-ID pairs is corresponding to one of additional terms, frequent scientific terms, and undesirable terms. Based on the analysis, a remove-term file is generated using the one or more term-ID pairs. Further at least one term-ID pairs from among the one or more term-ID pairs present in the remove-term file is altered to obtain modified term-ID pairs. Furthermore, the modified term-ID pairs may be added to an add-term file and a modified file may be obtained based at least on the remove-term file and the add-term file. Additionally, duplicate term-ID pairs present in the modified file may be removed to obtain the dictionary of scientific terms.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings for reference to like features and components.

DETAILED DESCRIPTION

Systems and methods for creation of a dictionary of scientific terms are described herein. Generally, research in the field of natural sciences, such as genetics, chemicals, proteins, diseases, and anatomy requires studying not only experimental results related to a current research but also research material available online or stored in related databases. For instance, a person doing research on a particular organism's genome, such as human genome and rice genome may need to study previous researches on the genome and genes related to the particular genome. A genome, as will be understood is the entirety of an organism's hereditary information and contains all of the biological information needed to build and maintain a living example of that organism. The biological information contained in a genome is encoded in its deoxyribonucleic acid (DNA) and is divided into discrete units called genes. To study a particular genome a researcher may thus need to study gene data related to all or some genes associated with that genome. For example, in order to do research on tumor suppression in humans, a researcher may need to study gene data related to tumor suppressor gene, such as an adenomatous polyposis coli (APC) gene and a tumor protein 53 (TP53) gene is classified as a tumor suppressor gene.

Conventionally, various named entity recognition techniques have been implemented to search gene data related to a particular gene based on a gene name of the gene. The gene databases typically organize information by assigning unique identifiers to genes and proteins. For well-studied organisms, several databases can be consulted from either organism specific databases like the *Saccharomyces* Genome Database, FlyBase, Mouse Genome Informatics, and Rat Genome Database, or general gene databases like Entrez Gene and the manually curated gene and protein collection Swiss-Prot. These databases are quite diverse in terms of organism-specificity, structure, and applied curation procedure. Further, besides sequences, biochemical properties, and other information, these databases also contain gene names and protein names. Gene data may thus be searched from these gene databases and various sources of biomedical literature using easy to search and small in size identifiers, such as gene names, thus increasing the search efficiency and accuracy.

However, in absence of a common nomenclature paradigm for a gene name, identifying a gene based on the gene name may not be feasible using a gene name known to a researcher or a gene name used by the gene databases to store the gene. Thus, the generation and assignment of names to newly identified genes is not strictly standardized and every researcher is free to define, assign, and use names based on personal preferences. For instance, a person may use the year of his research as a gene name, while another person may use his lab's name as a gene name for the same gene. Thus, most genes are referred to by several names, i.e., synonyms are being used for the same gene, thus reducing search efficiency. Further, a name can be associated with several genes thus causing ambiguity in search results. Furthermore, gene names or symbols may overlap with general English words, such as the gene names leg, white, and key are English language words used in day to day life.

In order to increase the search efficiency, various tools, such as text mining tools or gene name dictionaries may be used to obtain the gene data. The text mining tools are typically based on machine learning rules to identify and obtain the gene data and may thus not be efficient due to lack of artificial intelligence. Dictionaries on the other hand are compilations of various names, i.e., synonyms gathered from various data sources, such as database or free text for a given gene. However, creating and maintaining a dictionary can be a cumbersome task owing to the rapid rate of genomic research. For instance, it is practically difficult to have up-to-date terminologies that are produced and curated manually by researchers as free text. Further, due to the use of either same gene name for different genes or common English terms as gene names creating a gene name dictionary in an automatic fashion becomes burdensome.

Similarly a researcher doing research in other fields of natural science, such as proteins, chemicals, drugs, and enzyme may need to search data related to such terms. For instance, in order to search data related to proteins, a person may use the protein structure or protein name known to him. However, name based search may not provide an efficient result as every researcher may not use the same name to refer to a particular protein. Further, maintaining a dictionary for scientific terms, such as proteins or chemical and drug names too may be a be a cumbersome task owing to the rapid rate of research in these and other fields of natural sciences, such as proteins, chemical and drugs, enzymes, diseases, symptoms, biological processes, molecular functions, localization, experimental methods, cell lines, cell type, tissues, anatomy, a taxonomy, and bioinformatics.

The present subject matter describes methods and systems for creation of a dictionary of scientific terms. According to an embodiment of the present subject matter, input data having data related to a particular field of natural sciences is obtained, for example, from a scientific database having a collection data related to the field of natural sciences under consideration. For example, input data having data related to various chemicals and drugs may be downloaded from a chemical and drug database. Similarly, gene data related to genes associated with a genome, such as human genome, mouse genome, and rice genome may be obtained from a gene database having a collection of gene data obtained from various sources.

The input data may then be filtered to obtain a primary file having a plurality of scientific terms and a plurality of term IDs, such that each of the scientific terms and its corresponding term ID are provided in the form of term-ID pairs. For example, the gene data may be filtered to obtain a primary file having a plurality of gene names and a plurality of gene IDs, such that each of the gene names and its corresponding gene ID are provided in the form of gene name-ID pairs.

The primary file is subsequently analyzed to obtain a remove-term file having term-ID pairs corresponding to at least one of additional terms, frequent scientific terms, and undesirable terms. Additional terms may be understood as terms that are general English terms used in day-to-day life, such as leg, white, and key and include terms used in fields of natural science other than the field of natural science under consideration. Similarity of the scientific terms with such additional terms may lead to unwanted search results, thus reducing the efficiency of search based on the dictionary of scientific terms. For instance, in the previous example of gene data, the remove-term file may include gene name-ID pairs corresponding to at least one of the additional terms, frequent gene names, and the undesirable terms. Further, the additional terms may include general English terms, and names of diseases and symptoms. In one implementation, the primary file is compared with a list of the additional terms to identify all term-ID pairs having the additional terms as scientific terms. The term-ID pairs corresponding to the additional terms are copied to a remove-term file. Further, a predefined suffix, say, 'gene' in the case of genomic data is added to the additional term in each of the term-ID pairs to obtain modified term-ID pairs. The modified term-ID pairs may then be added to an add-term file.

Frequent scientific terms may be understood as the scientific terms that are associated with more than a predetermined number of term IDs. In one implementation, a scientific term associated with more than six different term IDs may be identified as a frequent scientific term. Term-ID pairs corresponding to the frequent scientific term are subsequently added to the remove-term file. For instance, in the above example of gene data, a gene name associated with more than six different gene IDs may be identified as a frequent gene name and gene name-ID pairs corresponding to the frequent gene name may be added to the remove-term file.

Undesirable terms may be understood as the terms that are not considered, based on some predefined conditions, to be genuine or preferred scientific terms used in the field of natural science under consideration. Term-ID pairs having the undesirable terms as scientific term may thus be added to the remove-term file. For instance, in the previous example of gene data, undesirable terms may be understood as the terms that are not considered to be genuine or preferred gene names.

The primary file may then be modified based on the add-term file and the remove term-file. In one implementation, entire content of the primary file is converted to lower case characters to ensure uniformity in scientific terms and also to enable identification of duplicate term-ID pairs. Subsequently, all term-ID pairs present in the remove-term file are removed from the primary file to obtain an intermediate file. Further, all term-ID pairs present in the add-term file are added to the intermediate file to obtain a, modified file, such as a modified file in the case of gene data as discussed above.

The modified file, in one implementation, may be further edited to remove certain term-ID pairs that may be recognized as invalid based on, for example, review from users of the input data or expert researchers. Additionally, certain term-ID pairs corresponding to scientific terms that are expected to be in a certain character case are replaced by term-ID pairs in the specific case. Further, all duplicate term-ID pairs may be removed from the modified file to obtain a dictionary of scientific terms having unique term-ID pairs. For instance, in the example discussed previously, the modified file may be further edited to obtain a gene name dictionary having unique gene name-ID pairs.

The present subject matter thus discloses an easy, faster, and efficient method and system for creating a dictionary of scientific terms, such as a gene name dictionary. Creating various intermediate files, such as add-term file and remove-term enables the system to automatically create and update the dictionary of scientific terms. For instance, whenever a new scientific term is identified to be associated with a particular term ID, the same may be updated in the add-term file and used by the system to update the dictionary of scientific terms, for example, during a periodic update event.

Although the description herein is provided in considerable detail with respect to creation of a gene name dictionary based on gene data, it will be understood that the methods and systems for dictionary creation can be implemented for creating dictionaries of scientific terms related to other fields of natural sciences, for example, but not limited to, chemicals, drugs, proteins, anatomy, enzymes, diseases, and bioinformatics as well, albeit with a few variations, as will be understood by a person skilled in the art.

While aspects of described systems and methods for creation of a dictionary of scientific terms can be implemented in any number of different computing systems, environments, and/or configurations, the embodiments are described in the context of the following exemplary system(s).

Figure 1:
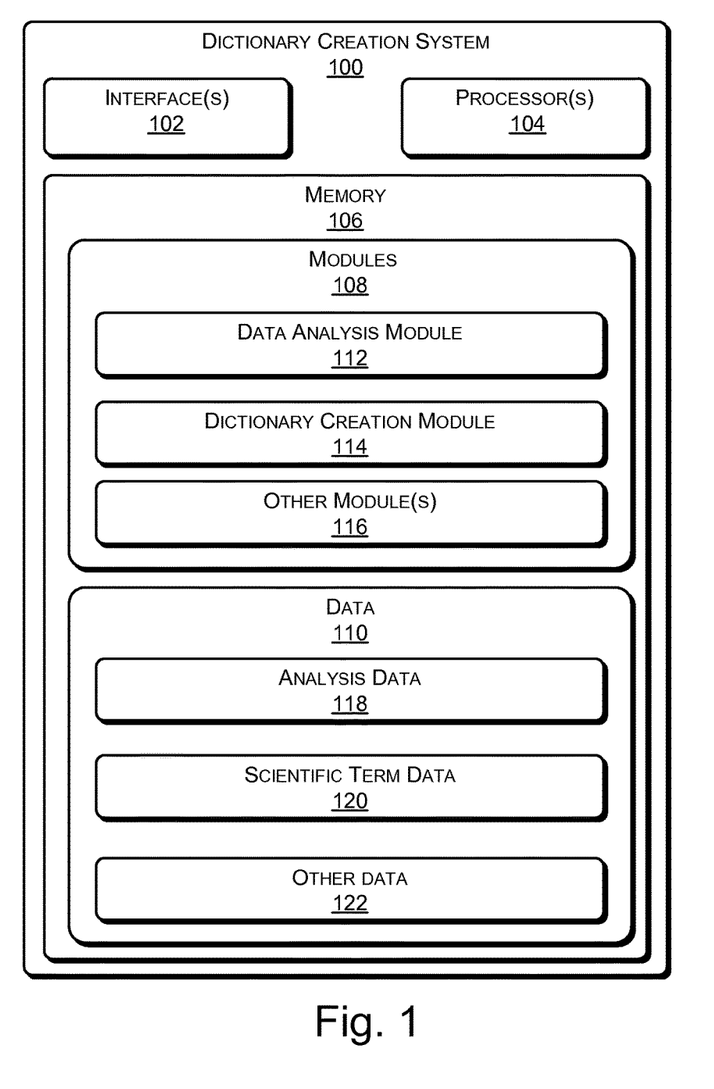
FIG. 1 illustrates a system for creation of a dictionary of scientific terms, in accordance with an embodiment of the present subject matter.

FIG. 1 illustrates a dictionary creation system 100, according to an implementation of the present subject matter. The dictionary creation system 100 is configured to obtain a dictionary of scientific terms having a plurality of term-ID pairs, such that each of the term-ID pairs includes a scientific term and a unique term ID associated with the scientific term. It will be understood that a unique term ID may be repeated across multiple term-ID pairs as the unique term ID may be associated with more than one scientific terms. The dictionary creation system 100 can be implemented in systems that include, but are not limited to, desktop computers, hand-held devices, multiprocessor systems, personal digital assistants (PDAs), laptops, network computers, cloud servers, minicomputers, mainframe computers, and the like. In one implementation, the dictionary creation system 100, hereinafter referred to as, the system 100 includes interface(s) 102, one or more processor(s) 104, and a memory 106 coupled to the processor(s) 104.

The interfaces 102 may include a variety of software and hardware interfaces, for example, interfaces for peripheral device(s), such as a keyboard, a mouse, an external memory, and a printer. Further, the interfaces 102 may enable the system 100 to communicate with other devices, such as web servers and external databases. The interfaces 102 can facilitate multiple communications within a wide variety of networks and protocol types, including wired networks, for example, local area network (LAN), cable, etc., and wireless networks, such as Wireless LAN (WLAN), cellular, or satellite. For the purpose, the interfaces 102 may include one or more ports for connecting a number of computing systems with one another or to another server computer.

The processor(s) 104 can be a single processing unit or a number of units, all of which could include multiple computing units. The processor 104 may be implemented as one or more microprocessors, microcomputers, microcontrollers, digital signal processors, central processing units, state machines, logic circuitries, and/or any devices that manipulate signals based on operational instructions. Among other capabilities, the processor 104 is configured to fetch and execute computer-readable instructions and data stored in the memory 106.

The memory 106 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 106 also includes module(s) 108 and data 110.

The modules 108, amongst other things, include routines, programs, objects, components, data structures, etc., which perform particular tasks or implement particular abstract data types. The modules 108 further include a data analysis module 112, a dictionary creation module 114, and other module(s) 116. The other modules 116 may include programs that supplement applications on the system 100, for example, programs in the operating system. On the other hand, the data 110 serves, amongst other things, as a repository for storing data processed, received, and generated by one or more of the modules 108. The data 110 includes analysis data 118, scientific term data 120, and other data 122. The other data 122 includes data generated as a result of the execution of one or more modules in the other modules 116.

In one implementation, the system 100 is associated with a scientific database (not shown in the figure). Examples of the scientific database include, for the purpose of illustration and not as a limitation, a gene database, such as Entrez Gene database; a protein database, such as UniProt KB database; a chemical and drugs databases, such as MeSH database; an enzymes database, such as Expasy Enzyme database; a disease name database, such as MeSH database; a symptom database, such as MeSH database; a biological process database, such as Gene Ontology database; a molecular function database, such as Gene Ontology database, a localization database, such as Gene Ontology database, an experimental method database, such as MeSH database; a cell line database, such as HyperCLDB database; cell type database, such as MeSH database; a tissue database, such as MeSH database; an anatomy database, such as MeSH database; a taxonomy database, such as NCBI Taxonomy database; and a bioinformatics database.

The scientific database typically includes data related to a corresponding field of natural sciences. For instance, the gene database, such as Mouse Genome Informatics, Entrez Gene, and Swiss-Prot may include gene data related to genomes of one or more organisms, such as mouse genome, human genome, and rice genome. Similarly, the protein databases, such as UniProt KB may include protein data related to one or more proteins, while the chemical and drugs databases, such as MeSH may include chemical and drug data related to one or more chemicals and drugs. Further, each of the scientific databases includes, amongst other data, a plurality of scientific terms related to the associated field of natural science. Examples of the scientific term include, for the purpose of illustration and not as a limitation, gene names, protein names, chemical and drug names, enzyme names, disease names, symptoms, biological process names, molecular function names, localization terms, experimental method terms, cell line names, cell type names, tissue names, anatomy names, taxonomy names, and bioinformatics terms.

Although the description herein is provided in considerable detail with respect to creation of a gene name dictionary based on gene data, it will be understood that the methods and systems for dictionary creation can be implemented for creating dictionaries of scientific terms related to other fields of natural sciences, such as chemicals, drugs, proteins, anatomy, enzymes, diseases, and bioinformatics as well, albeit with a few variations, as will be understood by a person skilled in the art.

The input data, as will be understood, includes data related to a particular field of natural sciences under consideration and is obtained by the system 100 for creating a dictionary of scientific terms. For instance, the gene data may include data related to various genes associated with a genome and is obtained by the system 100 for creation of a gene name dictionary for a particular genome. In one implementation, the gene data may include data such as "gene name", "symbol", "Locus tag", "synonyms", "description", "symbol from nomenclature", "full name from nomenclature", "taxonomic ID", and "other designations". Although the description of the system and the methods herein is in considerable detail with respect to gene data related to human genome, it will be understood that the methods and systems for creation of gene name dictionary can be implemented for other genomes, such as rice genome, mouse genome, *Arabidopsis thaliana* genome, and puffer fish genome as well, albeit with a few variations, as will be understood by a person skilled in the art.

In one implementation, the gene data may be identified and obtained by the data analysis module 112 based on a taxonomic ID. The taxonomic ID, as will be understood, is unique for each genome and thus helps in identifying the genome with which the gene is associated. For example, gene data corresponding to all the genes associated with the human genome may be identified by the data analysis module 112 based on the taxonomic ID of the human genome. In one implementation, the data analysis module 112 may connect to the gene database, say the Entrez Gene database and perform a search for all the genes having the taxonomic ID same as the human genome. The data analysis module 112 may obtain gene data related to all the genes identified based on search and store the gene data in the analysis data 118. Although the description herein is in considerable detail with respect to the gene data obtained from the Entrez Gene database, it will be understood that the methods and systems for creation of gene name dictionary can be implemented for gene data obtained from other file gene databases as well, albeit with a few variations, as will be understood by a person skilled in the art.

The data analysis module 112 may subsequently filter the input data, i.e., the gene data in the case of genomics to obtain a primary file having the plurality of scientific terms, such as a plurality of gene names and a plurality of term IDs, such as gene IDs. In one implementation, each of the scientific terms, such as gene names and its corresponding term ID, i.e., the gene ID are provided in the form of term-ID pairs, such as gene name-ID pairs. For exemplary purposes, and not as a limitation, the data analysis module 112 may obtain a primary file as illustrated in Table 1 below.

TABLE 1

| Gene ID | Gene Name |
|---------|-----------|
| 4014 | lor |
| 5023 | ATP receptor |
| 5024 | ATP receptor |
| 5025 | ATP receptor |
| 5027 | ATP receptor |
| 5028 | ATP receptor |
| 5029 | ATP receptor |
| 9127 | ATP receptor |
| 22953 | ATP receptor |
| 2537 | 6-16 |
| 3371 | 150-225 |
| 3543 | 14.1 |
| 3544 | 16.2 |
| 38 | T2 |
| 43 | YT |
| 9545 | gov |
| 9463 | pick |
| 11094 | flower |
| 27022 | genesis |
| 55364 | impact |
| 78996 | mri |
| 324 | adenomatous polyposis coli |
| 6261 | central core disease of muscle |
| 324 | apc |
| 324 | dp3 |
| 572 | BAD |
| 572 | bbc2 |
| 572 | bcl2-associated agonist of cell death |
| 637 | BID |
| 637 | fp497 |
| 637 | mgc15319 |
| 637 | mgc42355 |
| 637 | Bid |
| 820 | CAMP |

In the above example, various gene names have been listed in the column named "Gene Name", while a gene ID has been listed in the column named "Gene ID" such that corresponding gene name and gene ID are listed in the same row so as to form a term-ID pair.

Further, the data analysis module 112 may analyze the primary file to obtain intermediary files, such as an add-term file, a remove-term file, and a retain-case file. The remove-term file may be defined to include all term-ID pairs, such as gene name-ID pairs that may not be required in the gene name dictionary and may thus be removed from the primary file. The add-term file may be defined to include all term-ID pairs that need to be added to the gene name dictionary. The retain-case file may be defined to include all the term-ID pairs for whom the gene name has to be added in a predefined format in the gene name dictionary.

In one implementation, the data analysis module 112 analyzes the primary file to obtain term-ID pairs that need to be added to the remove-term file. For instance, the data analysis module 112 may identify all the term-ID pairs corresponding to at least one of additional terms; frequent scientific terms, such as frequent gene names; and undesirable terms as the term-ID pairs to be added to the remove-term file. In one implementation, additional terms may be understood as terms that are general English dictionary terms used in day-to-day life, such as flower, pick, and impact. Further, the terms may include terms used in fields of natural sciences other than the field under consideration, for instance, in the case of genomics the additional terms may include names of diseases and symptoms. Presence of such additional terms may lead to unwanted search results reducing the efficiency of gene data search and may thus be removed from the gene name dictionary. To identify the term-ID pairs corresponding to the additional terms, the data analysis module 112 may compare the primary file with a list of the additional terms to identify all term-ID pairs having the additional terms as gene names. The term-ID pairs corresponding to the additional terms may then be copied by the data analysis module 112 to the remove-term file.

For instance, in the above referred example, the data analysis module 112 may identify the term-ID pairs: "55364-impact", "78996-mri", and "324-adenomatous polyposis coli" as term-ID pairs that may not be required in the gene name dictionary.

Frequent scientific terms may be defined as the scientific terms having a cross-ID reference of more than a predetermined value. For instance, genes names having a cross-ID reference of more than a predetermined value may be identified as the frequent gene names. Cross-ID referencing of a gene name may be understood as a situation where a particular gene name has been used for more than one gene ID. Cross-ID referencing may thus make a gene name based search for gene data less effective as gene data of additional genes may also appear in the search results. The data analysis module 112 may parse the primary file to determine all the gene names that have a cross-ID reference of more than a predetermined value as the frequent gene names. In one implementation, the analysis module may determine a gene name associated with more than six different gene IDs as a highly ambiguous gene name. Further, the data analysis module 112 identifies all term-ID pairs corresponding to the frequent gene name and subsequently adds the identified term-ID pairs to the remove-term file.

For instance, in the previous example of the primary file, the data analysis module 112 may identify the gene name "ATP receptor" as a frequent gene name and copy all the term-ID pairs having the gene name "ATP receptor", as illustrated in table 2.

TABLE 2

| Gene ID | Gene name |
| --- | --- |
| 5023 | ATP receptor |
| 5024 | ATP receptor |

TABLE 2-continued

| Gene ID | Gene name |
| --- | --- |
| 5025 | ATP receptor |
| 5027 | ATP receptor |
| 5028 | ATP receptor |
| 5029 | ATP receptor |
| 9127 | ATP receptor |
| 22953 | ATP receptor |

The data analysis module 112 may further analyze the primary file to identify all undesirable terms, i.e., the terms that are, based on some predefined conditions, considered not to be genuine or preferred gene names. Examples of the undesirable terms include, but are not limited to, all two lettered, such as AZ and A1; single lettered, such as X and Y; and numerical terms, such as 29 and 09. The data analysis module 112 may ascertain all term-ID pairs having the undesirable terms as gene names and copy the ascertained term-ID pairs to the remove-term file.

Referring to the example discussed above, the data analysis module may identify the gene names "6-16", "14.1", "T2", and "YT" as undesirable terms and copy the term-ID pairs "2537-6-16", "3543-14.1", "38-T2", and "43-YT" to the remove-term file.

The data analysis module 112 may subsequently save the remove-term file in the analysis data 118. Further, to ensure that a new gene name is not missed out form the gene name dictionary, the data analysis module 112 may modify, based on modification rules, one or more term-ID pairs present in the remove-term file to obtain modified term-ID pairs. For instance, the data analysis module 112 may modify all the term-ID pairs corresponding to the additional terms to obtain the modified term-ID pairs. In one implementation, the data analysis module 112 may modify the term-ID pair by adding a predefined suffix, say, 'gene' to the scientific terms, such as the gene name in each of the term-ID pairs corresponding to the term-ID pairs copied to the remove-term file. In another implementation, the data analysis module 112 may modify the term-ID pair by expanding gene names that are abbreviations. In yet another implementation, the data analysis module 112 may modify the term-ID pair by changing case of all English dictionary words to capital cases. The data analysis module 112 may subsequently copy the modified term-ID pairs to the add-term file and save the add-term file in the analysis data 118.

For instance, in the above referred example, the data analysis module 112 may modify the term-ID pair "324-adenomatous polyposis coli" to obtain the modified term-ID pair "324-adenomatous polyposis coli gene".

Further, the data analysis module 112 may add few term-ID pairs in the add-term file based on user inputs. For instance, a researcher may desire to add few term-ID pairs, not present in the current primary file, but known to him due to his experience or latest research in the gene name dictionary. The data analysis module 112 may add all the user inputs to the add-term file. Configuring the data analysis module 112 to add term-ID pairs in the add-term file based on the user inputs helps in ensuring that the gene name dictionary includes all possible and known gene names corresponding to a gene. Further, using user inputs may facilitate quick and easy update of a gene name dictionary as new gene names identified in a latest research may be added to the add-term file for updating the gene name dictionary without going through the whole process of dictionary creation.

The data analysis module 112 may further add the term-ID pairs corresponding to gene names that have to be retained in a predefined format in the gene name dictionary. In one implementation, the data analysis module 112 may compare the primary file with a list of retain-case gene names to identify all the term-ID pairs having the retain-case gene names. The identified gene names may be added by the data analysis module 112 to the retain-case file saved in the analysis data 118.

The add-term file, the remove-term file, and the retain-case file may be subsequently used by the dictionary creation module 114 to modify the primary file to obtain a modified file. In one implementation, the dictionary creation module 114 removes all the gene name-ID pairs present in the remove-term file from the primary file to obtain an intermediate primary file. The intermediate file may be saved by the dictionary creation module 114 in the scientific term data 114. Further, the dictionary creation module 114 may convert to lower case all the gene names in the intermediate primary file.

The dictionary creation module 114 may then add all the term-ID pairs present in the add-term file to the intermediate file. For instance, the dictionary creation module 114 may add all the modified term-ID pairs, such as "324-adenomatous polyposis coli gene" to the intermediate file. Further, the dictionary creation module 114 may replace, using all the term-ID pairs present in the retain-case file, all term-ID pairs in the intermediate primary file whose gene names are desired to be in a particular case. Additionally, the dictionary creation module 114 may modify the intermediate file by removing all term-ID pairs identified, for example, by users as partially or completely incorrect or not genuine gene names. In one implementation, the dictionary creation module 114 may initially create a user review file based on user reviews received from one or more users or researchers accessing the gene dictionary or the gene data saved in the gene databases. All the term-ID pairs corresponding to such gene names present in the user reviews file may be reviewed based on domain experience and valid pairs may be identified and removed from the intermediate file by the dictionary creation module 114.

The modified file thus obtained may be saved by the dictionary creation module 114 in the scientific term data 120. Further, the dictionary creation module 114 may analyze the modified file to determine all duplicate term-ID pairs present in the modified file. All the duplicate term-ID pairs thus determined may be removed from the modified file by the dictionary creation module 114 to obtain the gene name dictionary. The gene name dictionary so created may be saved by the dictionary creation module 114 in the scientific term data 120. Thus, the system 100 may be configured to obtain the dictionary of scientific terms having a plurality of unique term-ID pairs, such that each of the unique term-ID pairs includes a scientific term and term ID associated with the scientific term.

Figure 2:
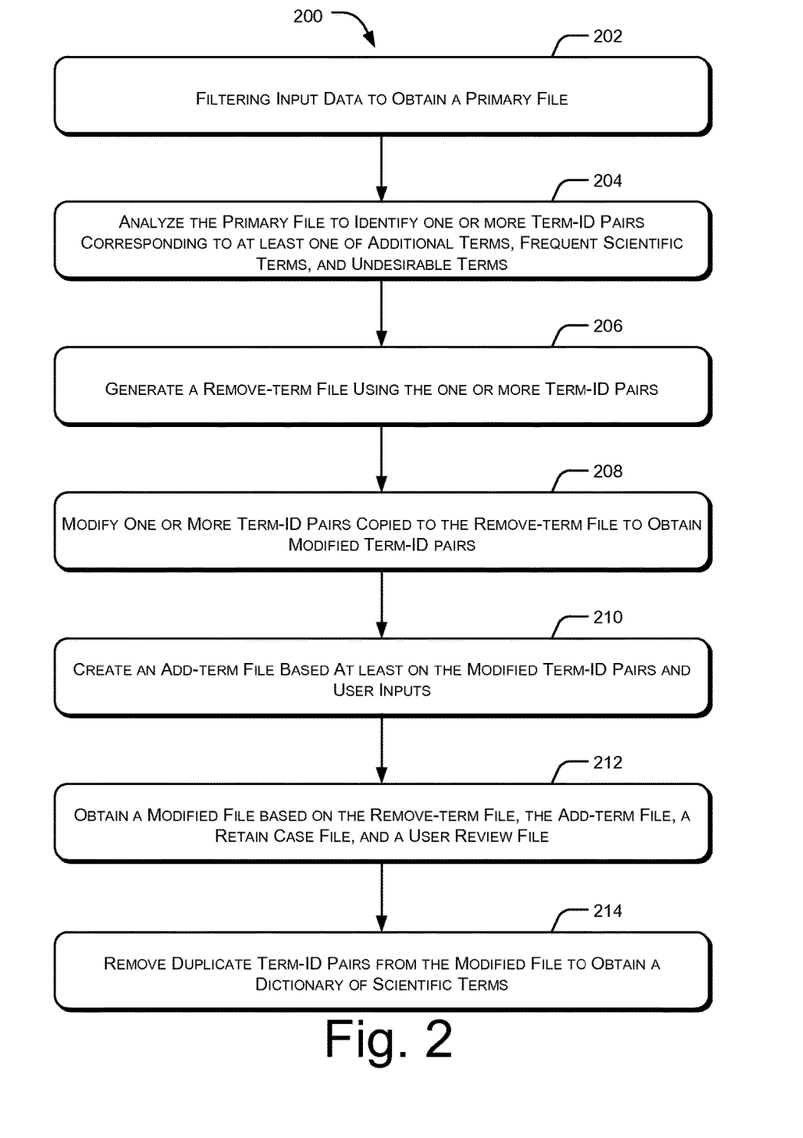
FIG. 2 illustrates a method for creation of a dictionary of scientific terms, in accordance with an embodiment of the present subject matter.

FIG. 2 illustrates a method 200 for creating a dictionary of scientific terms, such as a gene name dictionary, in accordance with an implementation of the present subject matter. The method 200 is implemented in computing device, such as the dictionary creation system 100. The method may be described in the general context of computer executable instructions. Generally, computer executable instructions can include routines, programs, objects, components, data structures, procedures, modules, functions, etc., that perform particular functions or implement particular abstract data types. The method may also be practiced in a distributed computing environment where functions are performed by remote processing devices that are linked through a communications network.

The order in which the method is described is not intended to be construed as a limitation, and any number of the described method blocks can be combined in any order to implement the method, or an alternative method. Additionally, individual blocks may be deleted from the method without departing from the spirit and scope of the subject matter described herein. Furthermore, the method can be implemented in any suitable hardware, software, firmware, or combination thereof.

At block 202, input data corresponding to a particular field of natural sciences is filtered to obtain a primary file. In one implementation, the input data is received, for example, by the system 100 from a scientific database. For example, gene data corresponding to a particular genome may be received from a gene database and filtered to obtain a primary file. The gene data, as may be understood, may include a polarity of data fields having information about various genes associated with the particular genome. The gene data may be received and saved, for example, in the analysis data 118 by an analysis module, for example, the data analysis module 112. Subsequently the input data may be filtered to obtain a primary file having two data fields, one for terms associated with the field under consideration and other for term IDs corresponding to the terms, such that corresponding term ID and term are listed in a single row, thus forming a term-ID pair. For instance, the gene data may be filtered to obtain a primary file having two data fields, one for gene IDs of genes associated with the genome and other for gene names corresponding to the gene IDs, such that corresponding gene ID and gene name are listed in a single row, thus forming a gene name-ID pair.

At block 204, the primary file having a plurality of term-ID pairs is analyzed for example, by the data analysis module 112. In one implementation, the primary file is analyzed to identify one or more term-ID pairs corresponding to at least one of additional terms, frequent scientific terms, and undesirable terms. For example, the primary file having a plurality of gene name-ID pairs may be analyzed to identify one or more gene name-ID pairs corresponding to at least one of additional terms, frequent gene names, and undesirable terms. In one implementation, the primary file may be compared with a list of additional terms to identify the additional terms. The frequent scientific terms may be determined based on frequency of cross-ID referencing, i.e., association of a particular term with more than one term ID. Term names having the cross-ID frequency of more than a predetermined value, for example, six may be identified as frequent scientific terms which may be ambiguous terms. Further, scientific terms that may be considered as undesirable scientific terms, say numerical terms and single lettered or two lettered terms may be identified as undesirable terms.

At block 206, a remove-term file may be generated using the one or more term-ID pairs identified at block 204. In one implementation, the data analysis module 112 may copy all the term-ID pairs corresponding to at least one of the additional terms, the frequent scientific terms, and the undesirable terms. For instance, in the previous example of gene data, a remove-term file may be generated using the one or more gene name-ID pairs identified at block 204. The remove-term file may be saved in the analysis data 118.

At block 208, one or more term-ID pairs copied to the remove-term file are modified to obtain one or more modified term-ID pairs. The one or more term-ID pairs copied in the remove-term file may be identified based on predetermined rules and modified to obtain the modified term-ID pairs, for example, by the data analysis module 112. In one implementation, for the term-ID pairs corresponding to the additional terms, the term-ID pair may be modified by adding a predefined suffix, say, 'gene' in the case of gene data at the end of the scientific terms in each of such term-ID pair. In another implementation, the data analysis module 112 may modify the term-ID pair by, for example, expanding gene names that are abbreviations or by changing case of all English dictionary words to capital cases. For instance, in the above example of gene data, one or more gene name-ID pairs copied to the remove-term file are modified to obtain one or more modified gene-ID pairs.

At block 210, an add-term file is created based at least on the modified term-ID pairs and user inputs. In one implementation, the data analysis module 112 may create the add-term file using the modified term-ID pairs obtained at block 210. Further, few term-ID pairs in the add-term file based on user inputs received from, for example, a researcher who may desire to add few term-ID pairs, not present in the current primary file, but known to him due to his experience or latest research in the field under consideration. For instance, in the previous example of gene data, an add-term file is created based at least on the modified gene-ID pairs and user inputs.

At block 212, a modified file is obtained based on the remove-term file, the add-term file, a retain case file, and a user review file. In one implementation, the primary file may be modified by a dictionary creation module, for example, the dictionary creation module 114 to obtain the modified file. For instance, in the above example of gene data, a modified file is obtained based on the remove-term file, the add-term file, a retain case file, and a user review file. Initially, all term-ID pairs present in the remove-term file are removed from the primary file to obtain an intermediate primary file. Scientific term of all the term-ID pairs present in the intermediate file is subsequently converted to lower case characters. Further, all terms present in the add-term file may be added to the intermediate file. The dictionary creation module 114 may then parse the retain-case file to determine all the term-ID pairs present in the retain-case file and replace using such term-ID pairs, corresponding term-ID pairs present in the intermediate file. Additionally, term-ID pairs present in the user review file may be removed from the intermediate file to obtain the modified file. In one implementation, the modified file may be saved in the scientific term data 120.

At block 214, duplicate term-ID pairs may be removed from the modified file to obtain a dictionary of scientific terms. In one implementation, the modified file is analyzed, for example, by the dictionary creation module 114 to identify all term-ID pairs occurring more than once in the modified file as the duplicate term-ID pairs. The duplicate term-ID pairs may be subsequently removed to create the dictionary of scientific terms. For instance, in the previous example of gene data, duplicate gene name-ID pairs may be removed from the modified file to obtain a gene name dictionary.

Although the description herein is provided in considerable detail with respect to creation of a gene name dictionary based on gene data, it will be understood that the methods and systems for dictionary creation can be implemented for creating dictionaries of scientific terms related to other fields of natural sciences, such as chemicals, drugs, proteins, anatomy, enzymes, diseases, symptoms, biological processes, molecular functions, localization, experimental methods, cell lines, cell types, tissues, taxonomy, and bioinformatics as well, albeit with a few variations, as will be understood by a person skilled in the art.

Although embodiments for creation of a dictionary of scientific terms have been described in language specific to structural features and/or methods, it is to be understood that the invention is not necessarily limited to the specific features or methods described. Rather, the specific features and methods are disclosed as exemplary embodiments for the creation of the dictionary of scientific terms.

We claim:
1. A method for automated creation of a dictionary of scientific terms comprising:
    filtering input data to obtain a primary file comprising a plurality of term-ID pairs, wherein the input data comprises data from one or more sources, and wherein each of the plurality of term-ID pair includes a unique term ID and a scientific term associated with the unique term ID;
    analyzing the primary file to generate a remove-term file, the remove-term file comprising one or more term-ID pairs from among the plurality of term-ID pairs, wherein the one or more term-ID pairs corresponds to one or more of additional terms, frequent scientific terms, and undesirable terms, and wherein the remove-term file is generated by comparing the primary file with a list of the additional terms to identify term-ID pairs having additional terms as scientific terms and copying the identified term-ID pairs corresponding to the additional terms to the remove-term file;
    and wherein the frequent scientific term is a scientific name associated with a predetermined number of term IDs, and wherein the additional term is a term not associated with a predetermined number of term IDs, and wherein the undesirable terms are non-scientific terms based on a predefined condition;
    altering, based on modification rules, at least one term-ID pair from among the one or more term-ID pairs present in the remove-term file to obtain at least one modified term-ID pair, wherein the at least one modified term-ID pair is copied to an add-term file, wherein the modification rules include at least one of adding a predetermined suffix, expanding abbreviated terms in the term-ID pair, and changing cases of terms in the term-ID pair;
    modifying the primary file, to obtain a modified file, based on the remove-term file and the add-term file, wherein the modified file is further modified to remove an invalid term-ID pair from one or more term-ID pairs; and
    removing duplicate term-ID pairs from the modified file to obtain the dictionary of scientific terms, the dictionary of scientific terms includes a plurality of term-ID pairs terms comprising at least one gene name dictionary for a particular genome including one or more gene name variation.

2. The method as claimed in claim 1, wherein the modifying comprises:
    removing, from the primary file, the one or more term-ID pairs present in the remove-term file to generate an intermediate file; and
    adding, to the intermediate file, the at least one modified term-ID pair present in the add-term file to obtain the modified file; and
    updating the intermediate file based on one or more term-ID pairs obtained from a retain case file.

3. The method as claimed in claim 2, wherein the modifying further comprises removing, from the intermediate file, one or more term-ID pairs present in a user review file.

4. The method as claimed in claim 3, wherein the modifying further comprises converting, in the intermediate file, all upper case characters to lower case characters.

5. The method as claimed in claim 1, wherein the altering comprises adding a predetermined suffix to the scientific term associated with a term-ID pair corresponding to the additional terms.

6. The method as claimed in claim 1, wherein the method further comprises,
updating the add-term file based on one or more user inputs; and
modifying the dictionary of scientific terms based on the updating.

7. The method as claimed in claim 1, wherein the scientific term comprises at least one of a gene name, a protein name, a chemical and drug name, an enzyme name, a disease name, a symptom, a biological process name, a molecular function name, a localization term, an experimental method term, a cell line name, a cell type name, a tissue name, an anatomy name, a taxonomy name, and a bioinformatics term.

8. The method as claimed in the claim 1, wherein the dictionary of scientific terms is obtained for the gene name variations comprising at least one of a symbol, a Locus tag, synonyms, description, a symbol from nomenclature, a full name from nomenclature and a taxonomic ID.

9. The method as claimed in claim 8, wherein the method further comprises obtaining, based on a taxonomic ID of a predetermined genome, gene data corresponding to the predetermined genome.

10. A dictionary creation system, the system comprising:
a processor; and
a memory coupled to the processor, the memory comprising:
a data analysis module configured to,
filter input data to obtain a primary file comprising a plurality of term-ID pairs, wherein the input data comprises data from one or more sources, and wherein each of the plurality of term-ID pair includes a unique term ID and a scientific term associated with the unique term ID;
generate a remove-term file based on one or more term-ID pairs identified from a primary file, wherein the scientific term of each of the one or more term-ID pairs corresponds to one or more of additional terms, frequent scientific terms, and undesirable terms, and wherein the remove-term file is generated by comparing the primary file with a list of the additional terms to identify term-ID pairs having additional terms pairs as scientific terms and copying the identified term-ID pairs corresponding to the additional terms to the remove-term file,
and wherein the one or more term-ID pairs are added to a remove-term file, wherein the frequent scientific term is a scientific name associated with a predetermined number of term IDs, and wherein the additional term is a term not associated with a predetermined number of term IDs, and wherein the undesirable terms are non-scientific terms based on a predefined condition; and
create an add-term file based on one of user inputs and at least one modified term-ID pair, wherein the at least one modified term-ID pair is obtained by modifying, based on modification rules, scientific terms associated with a term-ID pair selected from among the one or more term-ID pairs present in the remove-term file, wherein the modification rules include at least one of adding a pre-determined suffix, expanding abbreviated terms in the term-ID pair, and changing cases of terms in the term-ID pair; and
a dictionary creation module configured to,
modify the primary file, to obtain a modified file, based at least on the add-term file and the remove-term file, wherein the modified file is further modified to remove an invalid term-ID pair from one or more term-ID pairs; and
remove duplicate term-ID pairs from the modified file to obtain a dictionary of scientific terms, wherein the dictionary of scientific terms includes a plurality of term-ID pairs, comprising at least one gene name dictionary for a particular genome including one or more gene name variation.

11. The dictionary creation system as claimed in claim 10, wherein the dictionary creation module is configured to remove, from the primary file, the one or more term-ID pairs present in the remove-term file to generate an intermediate file.

12. The dictionary creation system as claimed in claim 11, wherein the dictionary creation module is configured to,
convert, in the intermediate file, all upper case characters to lower case characters; and
add, to the intermediate file, at least one modified term-ID pair present in the add-term file to obtain the modified file.

13. The dictionary creation system as claimed in claim 11, wherein the dictionary creation module is configured to,
add one or more term-ID pairs from a retain case file to the intermediate file; and
remove from the intermediate file, one or more term-ID pairs present in a user review file.

14. The dictionary creation system as claimed in claim 10, wherein the data analysis module is configured to analyze the primary file to identify a scientific name associated with more than the predetermined number of term IDs as the frequent scientific term for being removed from the primary file for creation of the dictionary of scientific terms.

15. The dictionary creation system as claimed in claim 10, wherein the data analysis module is configured to add a predetermined suffix to the scientific term associated with a term-ID pair corresponding to the additional terms to obtain the at least one modified term-ID pair.

16. The dictionary creation system as claimed in claim 10, wherein the scientific terms are selected from a group consisting of gene names, protein names, chemical and drug names, enzyme names, disease names, symptoms, biological process names, molecular function names, localization terms, experimental method terms, cell line names, cell type names, tissue names, anatomy names, taxonomy names, and bioinformatics terms.

17. A non-transitory computer-readable medium having embodied thereon a computer program for executing a method comprising:
filtering input data to obtain a primary file comprising a plurality of term-ID pairs, wherein the input data comprises data from one or more sources, and wherein each of the plurality of term-ID pair includes a unique term ID and a scientific term associated with the unique term ID;
analyzing a primary file to identify one or more term-ID pairs corresponding to at least one or more of additional terms, frequent gene names, and undesirable terms, wherein the scientific term of each of the one or more term-ID pairs corresponds to one or more of additional terms, frequent scientific terms, and undesirable terms, and wherein the one or more term-ID pairs are added to a remove-term file, wherein the frequent scientific term is a scientific name associated with a predetermined number of term IDs, and wherein the additional term is a term that is not associated with a predetermined number of term IDs, and wherein the undesirable terms are non-scientific terms based on a predefined condition;

generating a remove-term file using the one or more term-ID pairs by comparing the primary file with a list of the additional terms to identify term-ID pairs having additional terms as scientific terms and copying the identified term-ID pairs corresponding to the additional terms to the remove-term file;

modifying, based on modification rules, gene names of one or more term-ID pairs from among the term-ID pairs present in the remove-term file to obtain modified gene-ID pairs, wherein the modified gene-ID pairs are copied to an add-term file, wherein the modification rules include at least one of adding a pre-determined suffix, expanding abbreviated terms in the term-ID pair, and changing cases of terms in the term-ID pair;

obtaining a modified file based at least on the remove-term file and the add-term file; and removing duplicate term-ID pairs from the modified file to obtain the gene name dictionary for a particular genome including one or more gene name variation, wherein the modified file is further modified to remove an invalid term-ID pair from one or more term-ID pairs.

18. The non-transitory computer-readable medium as claimed in claim 17, wherein the modifying further comprising:

removing, from the primary file, the one or more term-ID pairs present in the remove-term file to generate an intermediate file; and adding, to the intermediate file, the at least one modified term-ID pair present in the add-term file to obtain the modified file; and updating the intermediate file based on one or more term-ID pairs obtained from a retain case file.

19. The non-transitory computer-readable medium as claimed in claim 17, wherein the method further comprises obtaining, based on a taxonomic ID of a predetermined genome, gene data corresponding to the predetermined genome.

20. The non-transitory computer-readable medium as claimed in claim 17, wherein the method further comprises:

updating the add-term file based on one or more user inputs; and modifying the dictionary of scientific terms based on the updating.

\* \* \* \* \*